(12) United States Patent
Pipe et al.

(10) Patent No.: US 8,512,386 B2
(45) Date of Patent: Aug. 20, 2013

(54) INFANT PHOTOTHERAPY DEVICE

(75) Inventors: Jeffrey Pipe, Pittsburgh, PA (US);
Richard J. Lordo, Butler, PA (US)

(73) Assignee: Ric Investments, LLC, Wilmington, DE (US)

( * ) Notice: Subject to any disclaimer, the term of this patent is extended or adjusted under 35 U.S.C. 154(b) by 1433 days.

(21) Appl. No.: 12/174,651

(22) Filed: Jul. 17, 2008

(65) Prior Publication Data
US 2009/0030490 A1 Jan. 29, 2009

Related U.S. Application Data

(60) Provisional application No. 60/961,754, filed on Jul. 24, 2007.

(51) Int. Cl.
*A61N 5/06* (2006.01)

(52) U.S. Cl.
USPC .......................................................... 607/91

(58) Field of Classification Search
USPC ................................ 607/88–94; 16/422, 430
See application file for complete search history.

(56) References Cited

U.S. PATENT DOCUMENTS

| | | | |
|---|---|---|---|
| 6,494,899 B1 | 12/2002 | Griffin et al. | |
| 6,596,016 B1 | 7/2003 | Vreman et al. | |
| 6,811,563 B2 | 11/2004 | Savage, Jr. et al. | |
| 6,861,658 B2 | 3/2005 | Fiset | |
| 6,872,220 B2 | 3/2005 | Williams et al. | |
| D506,831 S | 6/2005 | Miller et al. | |
| 6,955,684 B2 | 10/2005 | Savage, Jr. et al. | |
| 6,991,644 B2 | 1/2006 | Spooner et al. | |
| 7,081,128 B2 | 7/2006 | Hart et al. | |
| 7,125,416 B2 | 10/2006 | Kent et al. | |
| 7,131,990 B2 | 11/2006 | Bansal et al. | |
| 7,980,415 B2 * | 7/2011 | Crawley | 220/755 |
| 8,140,133 B2 * | 3/2012 | Jung et al. | 455/575.3 |
| 2001/0007080 A1 * | 7/2001 | Sheinman et al. | 607/91 |
| 2002/0198575 A1 * | 12/2002 | Sullivan | 607/88 |
| 2010/0095487 A1 * | 4/2010 | Gitman et al. | 16/430 |

OTHER PUBLICATIONS

Rosen, H. et al., "Use of a Light Emitting Diode (LED) Array for Bilirubin Phototransformation", Engineering in Medicine and Biology Society, 2005, IEEE-EMBS 2005, pp. 7266-7268.

\* cited by examiner

*Primary Examiner* — Sunil K Singh
(74) *Attorney, Agent, or Firm* — Timothy A. Nathan

(57) ABSTRACT

An infant phototherapy device comprises a housing assembly, a light source carried by the housing assembly, and a panel mode assembly including a panel mode adaptor arranged to be detachably connected with the housing assembly. The panel mode assembly further comprises an elongated flexible light pipe and a light emitting panel, the light pipe providing light communication between the light source and the light emitting panel, so that when the panel mode adaptor is connected with the housing assembly, light emitted by the light source is transmitted through the light pipe to the light emitting panel. A suspension structure is arranged to suspend the housing assembly, wherein when the panel mode adaptor is disconnected from the housing assembly and the housing assembly is suspended from the suspension structure, light emitted from the housing can be projected onto a patient.

15 Claims, 13 Drawing Sheets

200
INFANT PHOTOTHERAPY DEVICE

CROSS-REFERENCE TO RELATED APPLICATIONS

This application claims priority under 35 U.S.C. §119(e) from provisional U.S. patent application No. 60/961,754 filed Jul. 24, 2007, the entire contents of which are incorporated herein by reference.

BACKGROUND OF THE INVENTION

1. Field of the Invention

This invention relates to phototherapy devices and more particularly to infant phototherapy devices configured to provide phototherapy to infants.

2. Description of Related Art

Phototherapy devices that generate radiant energy, typically a visible light having a particular wavelength, and that transmit the energy to a surface of a patient are known. In one type of phototherapy device, light from a halogen bulb is transmitted to the surface of the patient to treat jaundice. An example of such a conventional phototherapy device is the Wallaby® phototherapy system distributed by Respironics Inc. of Pittsburgh, Pa.

Such conventional phototherapy devices typically include a source of illumination and a fiber optic cable having a proximal end coupled to the source of illumination for transmitting the light to the patient. A fiber optic panel is located at the distal end of the fiber optic cable to provide a blanket of light that can be positioned next to the patient's skin. The device is suitable to treat infants, especially newborns, who have jaundice.

SUMMARY OF THE INVENTION

The inventions herein provide several improvements over known phototherapy devices. In accordance with one aspect of the present invention, there is provided an infant phototherapy device comprising a housing assembly having a connection site; a light source carried within the housing assembly and constructed and arranged to emit light from the housing assembly; an enabling switch operable to enable and disable operability of the light source; a spotlight mode adaptor constructed to be selectively detachably connected with the housing assembly at the connection site, wherein attachment of the spotlight mode adaptor to the connection site changes the enabling switch from a disabling configuration to an enabling configuration and detachment of the spotlight mode adaptor changes the enabling switch from the enabling configuration to the disabling configuration, wherein when the spotlight mode adaptor is attached at the connection site, light from the light source may be emitted from the housing; and a panel mode assembly including a panel mode adaptor, the panel mode adaptor constructed and arranged to be detachably connected with the housing assembly at the connection site, the panel mode assembly including an elongated flexible light pipe connected at one end to the panel mode adaptor and at an opposite end to a light emitting panel, the panel mode assembly enabling light to be communicated from the light source through the flexible light pipe to the light emitting panel when the panel mode adaptor is attached to the connection site.

In accordance with another aspect of the present invention, there is provided an infant phototherapy device comprising a housing assembly, and an LED assembly constructed and arranged to emit light within the blue light spectrum; the LED assembly being mounted within the housing assembly between opposite ends thereof so as to emit light from one end of the housing assembly when energized; the housing assembly having a generally cylindrical outer surface, but with a central portion of a smaller diameter than at opposite portions thereof.

In accordance with another aspect of the present invention, there is provided an infant phototherapy device comprising a housing assembly, and an LED assembly which when energized provides a light source having an output in the blue light spectrum; the LED assembly being mounted within the housing assembly between opposite ends thereof; a circuit board electrically connected with the LED assembly mounted within the housing assembly along side the LED assembly; an on-off switch on the housing assembly electrically connected to said circuit board so as to control the energization of the LED assembly; the opposite ends of the housing assembly having inlet and outlet air passages therein, the LED assembly including LED mounting structures providing intermediate flow passages between the inlet and outlet passages, and a fan electrically connected to the circuit board and mounted within the housing assembly in a position to circulate air sequentially through the inlet, intermediate, and outlet passages.

In accordance with another aspect of the present invention, there is provided an infant phototherapy assembly comprising a manually portable housing assembly; an LED light source disposed within the housing assembly and capable of emitting light in the blue light spectrum; a bag-like structure constructed and arranged to removably securely contain the housing assembly therein without interfering with the light emitted exteriorly of the housing assembly by the LED light source; the bag-like structure including a mounting strap connected thereto.

In accordance with another aspect of the present invention, there is provided an infant phototherapy device comprising a housing assembly; a light source carried by the housing assembly; a panel mode assembly including a panel mode adaptor arranged to he detachably connected with the housing assembly, the panel mode assembly further comprising an elongated flexible light pipe and a light emitting panel, the light pipe providing light communication between the light source and the light emitting panel, so that when the panel mode adaptor is connected with the housing assembly, light emitted by the light source is transmitted through the light pipe to the light emitting panel; a suspension structure arranged to suspend the housing assembly, wherein when the panel mode adaptor is disconnected from the housing assembly and the housing assembly is suspended from the suspension structure, light emitted from the housing can be projected onto a patient.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

DETAILED DESCRIPTION OF THE EXEMPLARY EMBODIMENTS

Figure 1:
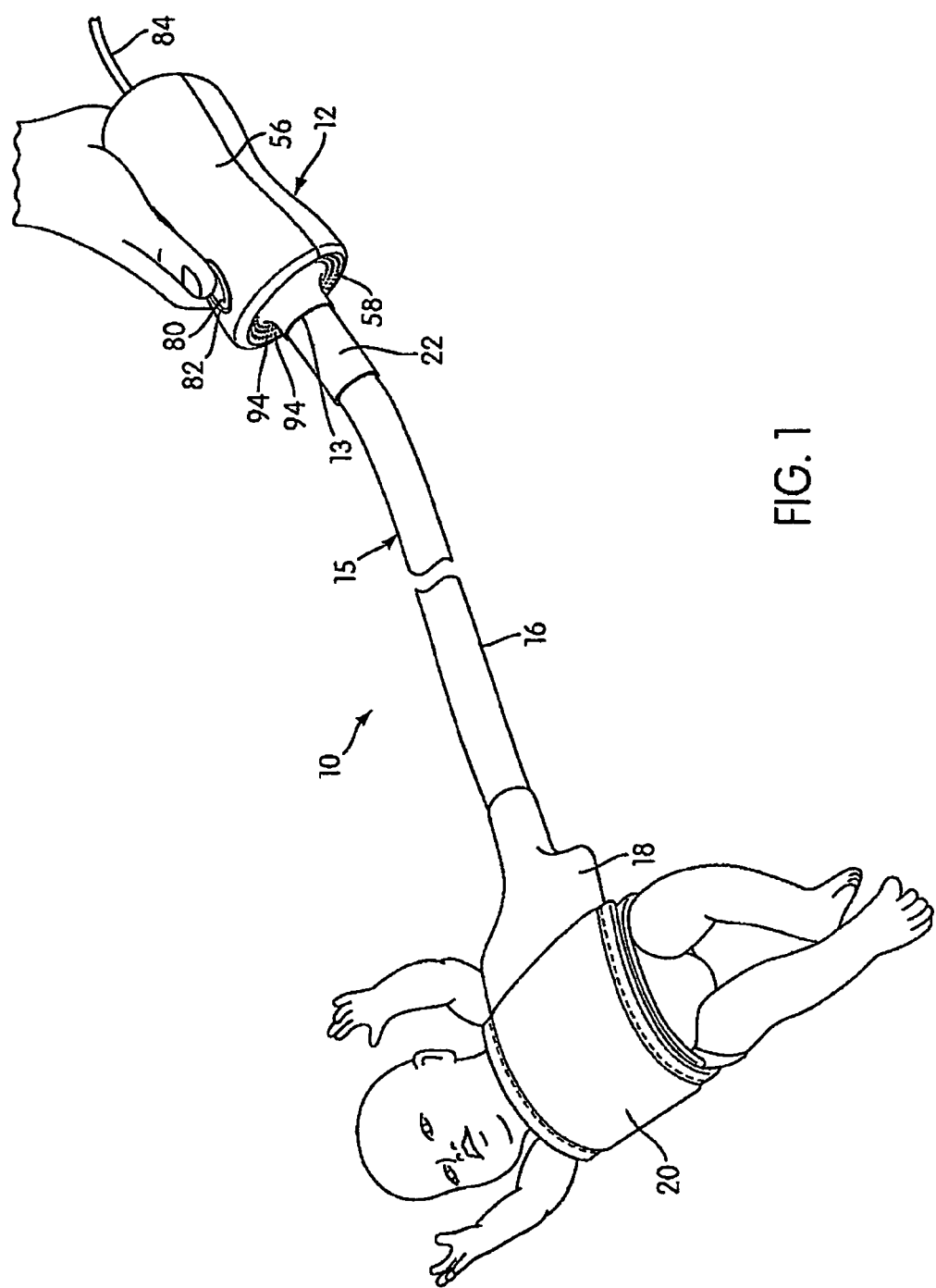
FIG. 1 is a perspective view of an infant phototherapy device embodying one aspect of the present, showing the device in its panel mode wrapped in relation to an infant.
Figure 5:
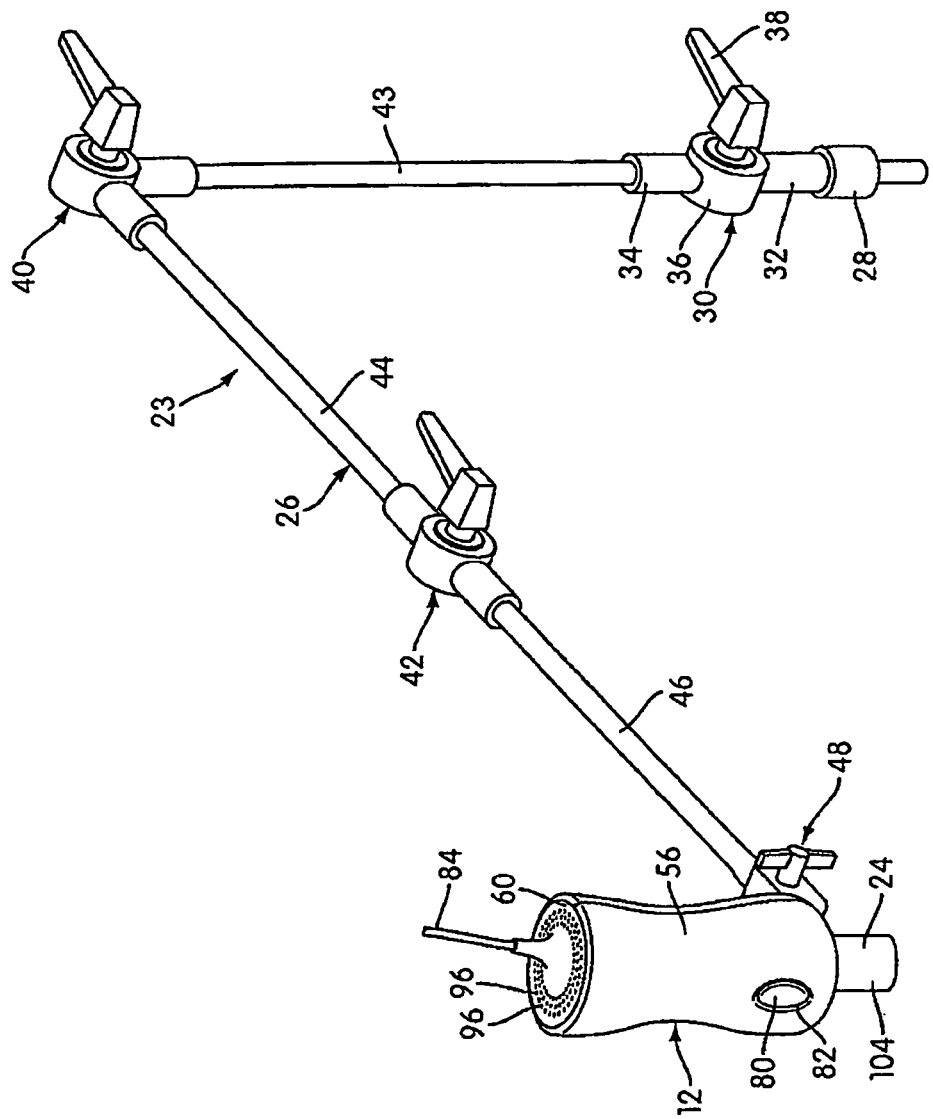
FIG. 5 is a perspective view of the device showing a suspension structure in a position of operation when the device is in a spotlight mode.

Referring now more particularly to the drawings, there is shown in FIG. 1 an infant phototherapy device, generally indicated at 10, which embodies various aspects of the present invention. The device 10 is operable selectively in one of two modes, a panel mode as illustrated in FIG. 1, and a spotlight mode as illustrated in FIG. 5.

Figure 2:
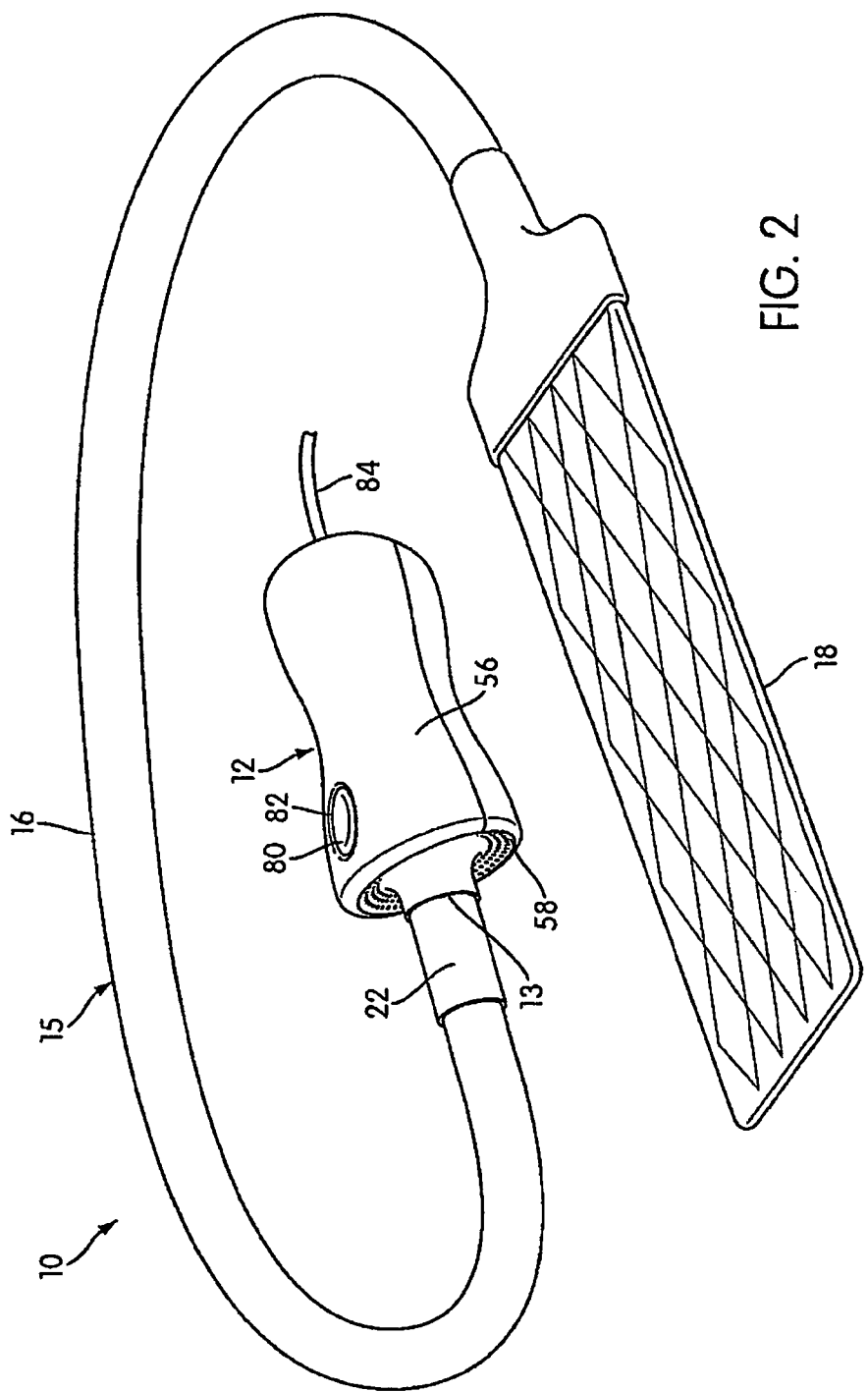
FIG. 2 is a perspective view of the infant phototherapy device itself.
Figure 9:
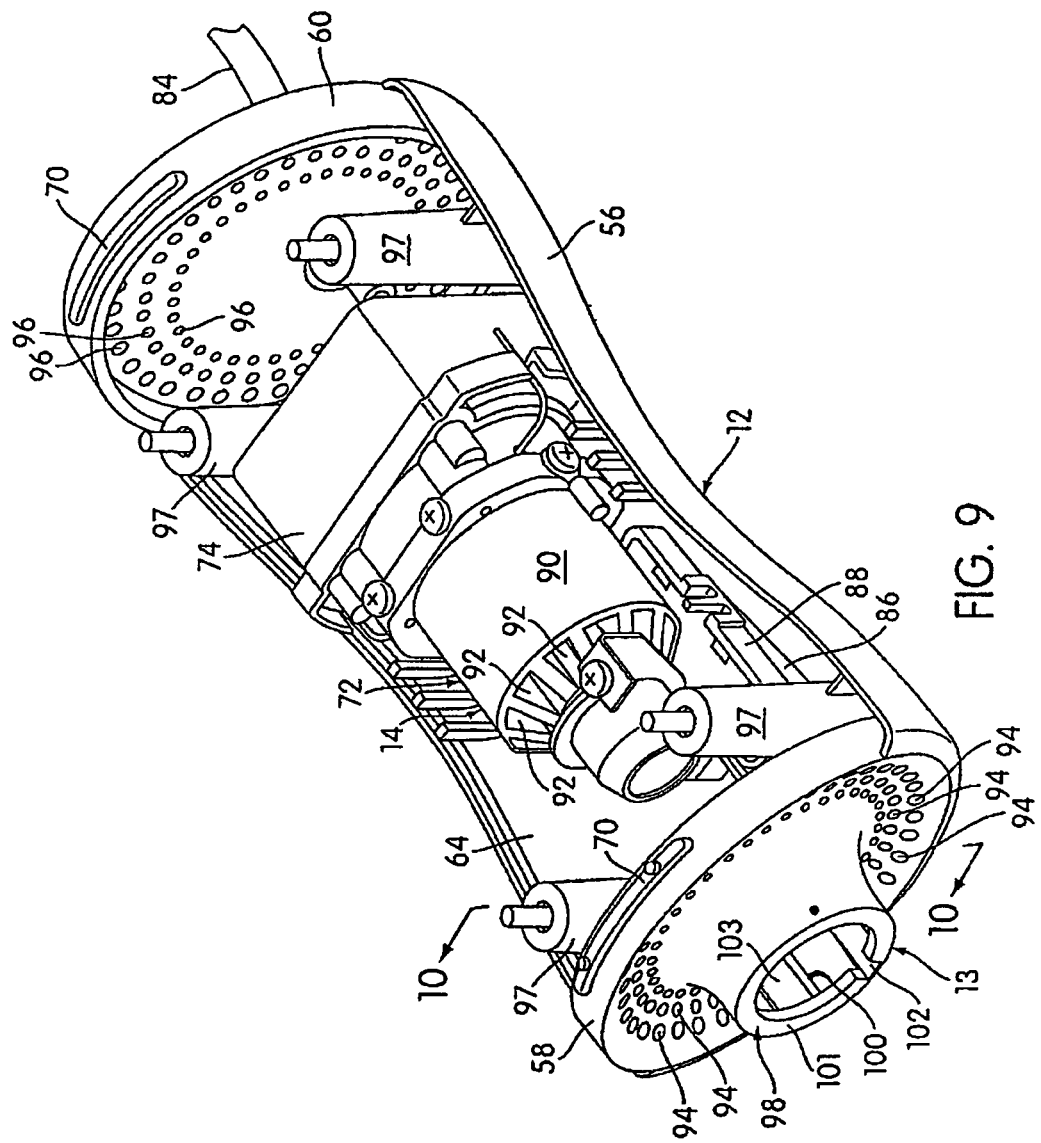
FIG. 9 is a perspective view of the housing assembly with the upper half-shell of the housing assembly removed to illustrate the interior parts within the housing assembly, the circuit board interior part also being removed for purposes of clearer illustration.
Figure 10:
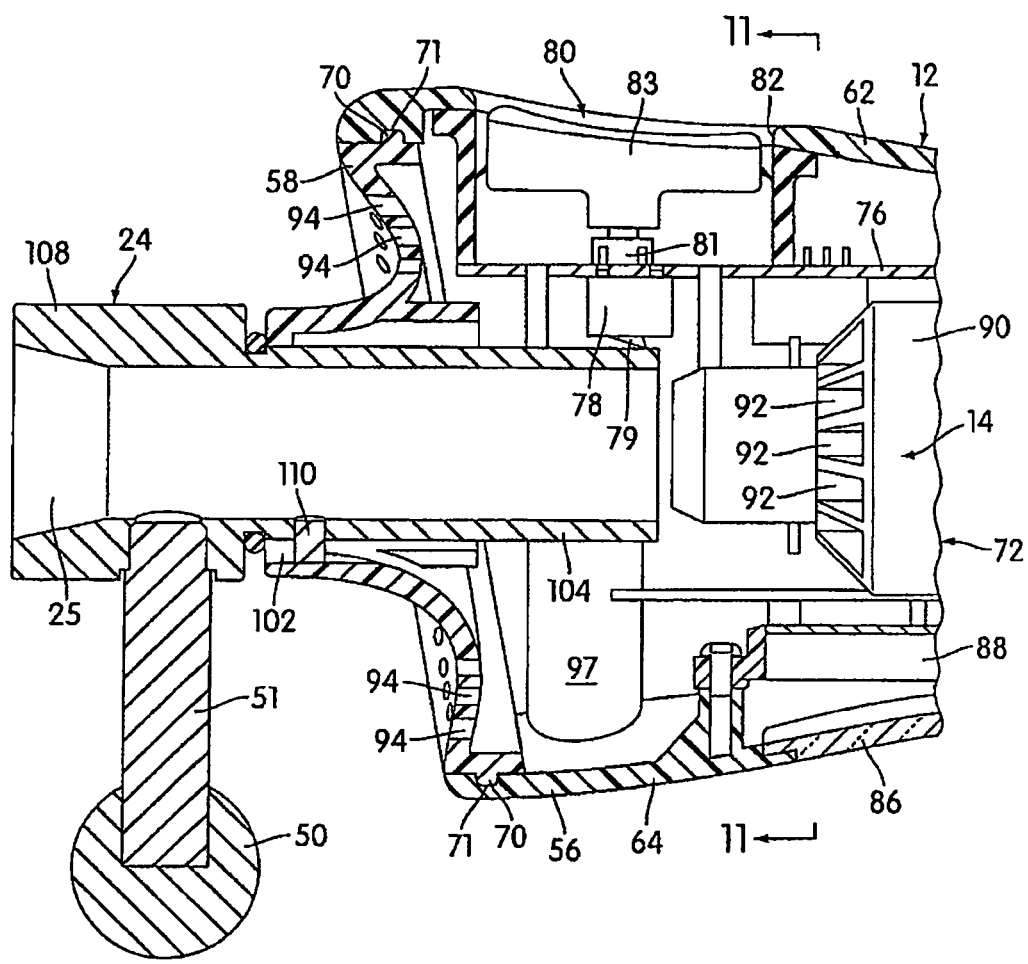
FIG. 10 is an enlarged fragmentary cross-sectional view taken along the line 10-10 of FIG. 9 showing the adaptor end portion of the housing assembly including the removed parts of FIG. 9, but with a spotlight mode adapter connected to the housing assembly.

The device 10, as shown in FIGS. 1-2, includes, in general, a housing assembly, generally indicated at 12, which contains a therapeutic light source 14 contained therein (see FIGS. 9 and 10). In one embodiment, the light source 14 may comprise one or more light emitting diodes (LEDs). The LED light source 14 may have an output intensity of greater than 55 $mW/cm^2/nm$, a lifespan greater than 600 hours, and emits wavelengths of light in the blue light spectrum. In one embodiment, the light source has an output of about 85 $mW/cm^2/nm$, and a lifespan of about 35,000 hrs. However, other known light sources useful in treating jaundice can also be used. For example, halogen or fluorescent light sources may be used, as disclosed in the '899 patent, for example.

When operated in the panel mode, as shown in FIG. 1, the device 10 includes panel mode assembly 15 including an elongated flexible light transmitting assembly or light pipe 16, a flexible light emitting panel assembly 18, and a panel mode adaptor 22. The panel mode adaptor 22 has a distal end that can be removably connected to the housing assembly 12 at a connection site 13, and in light transmitting relation with the light source 14 within housing assembly 12. The light from light source 14 can thus be communicated through the panel mode adaptor 22, which has a cylindrical configuration and hollow central passage, to the light pipe 16, and through the light pipe 16 to the panel assembly 18. In one embodiment, the light pipe 16 may comprise one or more fiber optic cables or chords. Both the light pipe 16 and the panel assembly 18 may be of the type known in the art, and as described in the aforementioned U.S. Pat. No. 6,494,899, incorporated by reference.

Figure 3:
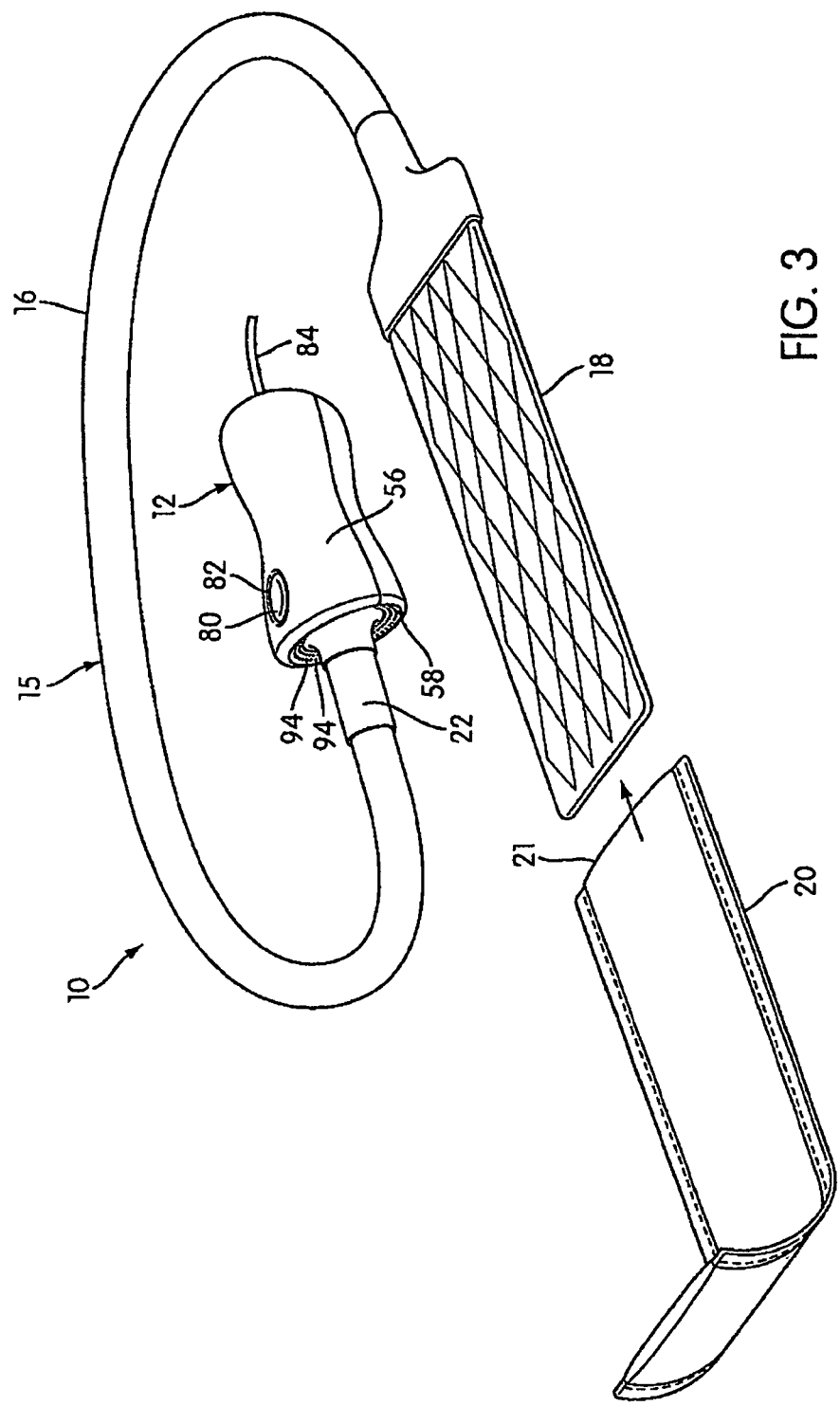
FIG. 3 is a perspective view similar to FIG. 2, and showing a panel sheath used to cover the panel assembly during treatment.

FIG. 3 illustrates a conventional, soft sheath or cover 20 having an opening 21 at one end thereof for receiving the panel assembly 18 therein in order to more comfortably accommodate the infant during treatment. The sheath or cover 20 is disposable, and may be permeable to light emitted from the panel 18 so that the light can be received by the skin of the infant.

As best shown in FIG. 1, the device 10, shown in its panel mode, is useful in treating jaundice in infants and particularly new born infants. The panel mode comprises wrapping the infant in the panel assembly 18 (optionally covered by sheath 20), and then energizing the light source 14 for a predetermined time period, as may be determined by a physician.

When in the panel mode, the panel mode adaptor 12 is used as the interface between the panel mode assembly 15 and the housing assembly 12, and in one embodiment can be used to enable an enabling switch as will be described later.

Figure 4:
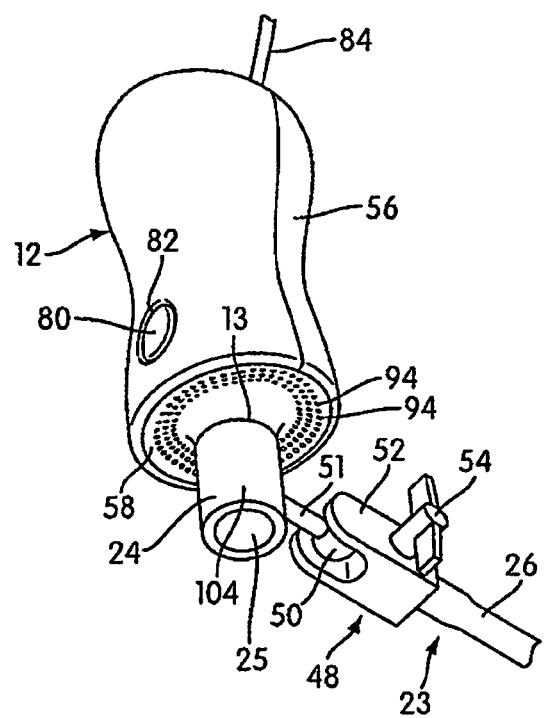
FIG. 4 is a perspective view illustrating the interface between the housing assembly of the device and a portion of suspension structure for use in a spotlight mode.

As best shown in FIGS. 4 and 5, when in the spotlight mode, a spotlight mode assembly 23 may be employed. The spotlight mode assembly 23 includes a spotlight adaptor, generally indicated at 24, and a suspension structure 26. The spotlight adaptor 24 connects with housing assembly 12 at connection site 13, and is used to connect the housing assembly 12 with the suspension structure 26. As shown in FIG. 5, the suspension structure 26 includes a mounting member 28 connected to an adjustable joint unit 30. The adjustable joint unit 30 includes a pair of sleeve like elements 32 and 34 pivotally interconnected by a pivot joint 36 therebetween. The pivot joint 36 can be released by turning a handle member 38 in one direction to allow interpivoting between the elements 32 and 34 and locked by turning the handle member 38 in the opposite direction to fix the elements 32 and 34 into the relative pivot positions into which they have been moved.

The suspension structure 26 includes two intermediate adjustable joint units 40 and 42, both constructed like the unit 30. Joint unit 40 is interconnected to the joint unit 30 by elongated tubular or rod-like member 43. Similarly, joint unit 42 is connected to joint unit 40 by tubular or rod-like member 44. The suspension structure 26 connects to the spotlight adaptor 24 by an adjustable universal joint unit 48. As shown in FIG. 4, the unit 48 includes a ball 50 fixed in spaced relation to the exterior of the spotlight adaptor 24 by a rod 51. The joint unit 48 also includes a movable jaw member 52 releasably secured to the ball 50 by an actuating handle 54. The joint unit 48 is connected to joint unit 42 by tubular or rod-like member 46.

When operated in the spotlight mode, the spotlight adaptor 24, when fixedly connected to the housing assembly 12 provides an opening 25 by virtue of its tubular construction (see FIGS. 4 and 10) for the passage of the light emitted by the light source 14. Proper direction of light emitted from the housing assembly when in the spotlight mode can be achieved by adjusting the adjustable units 30, 40, 42 and/or 48 after clamping the mounting member 28 in a fixed location relative to the bed, crib, or other mounting structure. The suspension structure 26 may take many different forms, as in one embodiment its only requirement is to suspend, hold, or position the housing assembly 12 for use in a spotlight mode (i.e., illuminating the skin of the infant without use of the panel mode assembly 15).

The housing assembly 12 can be of any suitable construction, shape, or configuration. In one embodiment, it is constructed to be light in weight (e.g., from molded plastic or elastomeric material) and easily carried from location to location in one hand. The housing assembly 12, as shown, has a generally smooth exterior gripping surface 56 disposed between opposite end members 58 and 60. The configuration of the gripping surface 56 is generally cylindrical or tubular between the opposite end members 58 and 60 of the housing assembly 12 and has a central portion of lesser circumferential dimension than at the opposite ends, enabling a user to easily grasp and hold the housing assembly 12 in manually portable fashion by one hand.

Figure 11:
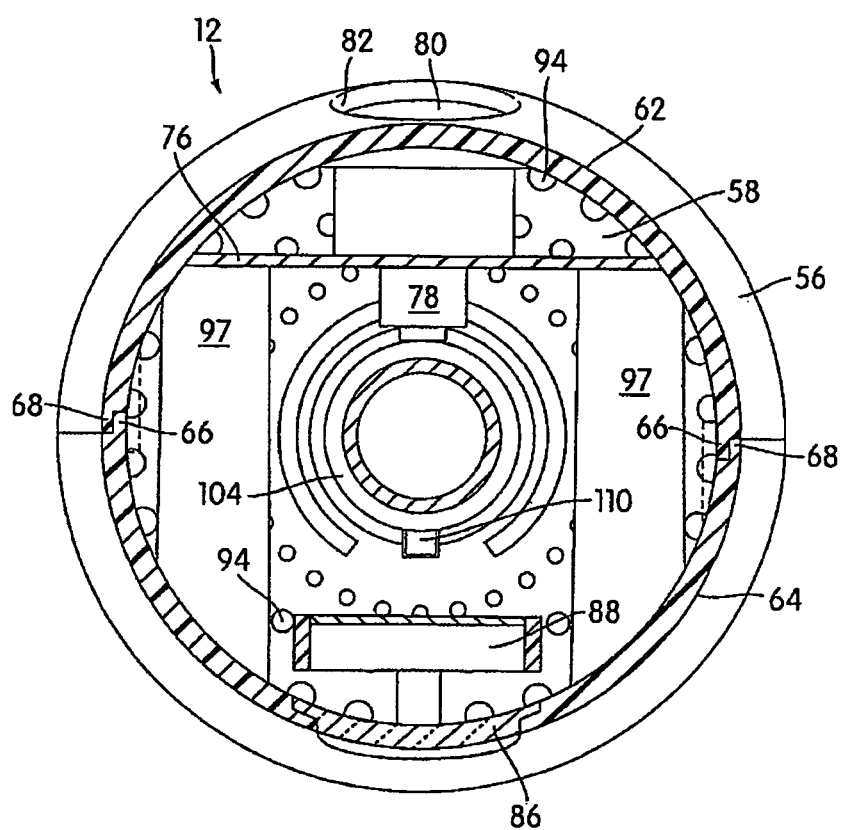
FIG. 11 is a cross-sectional view taken along the line 11-11 of FIG. 9 showing the interconnection of the lower housing half-shell with the upper housing half-shell.

As best shown in the embodiment of FIGS. 9 and 10, the structure of the housing assembly 12 which provides the gripping surface 56 comprises upper and lower molded plastic complimentary half-shells 62 and 64. As shown in FIG. 11, half-shells 62 and 64 have interengaging flanges 66 and 68 along the interengaging edges thereof. As seen in FIG. 10, the ends of the half-shells 62 and 64 are curved slightly inwardly to overlap the peripheral circumference of the associated end member 58 or 60 (only 58 shown in FIG. 10). Such ends have inner annular grooves 71 formed therein for receiving opposed annular projections 70 formed on the periphery of the end members 58 and 60. In one embodiment, the housing assembly 12 has an hourglass shape. Of course, a variety of other shapes may be utilized without departing from the teachings of the present invention. For instance, the device could have a stepped configuration, or even an ergonomic configuration which is configured to fit a user's hand. The hourglass shape provides two facing conical portions that may be easily grasped by a user. The larger end members reduce the opportunity for the device to slip out of the user's hand. In addition, the inventors contemplate that this shape may also be conveniently tucked under the users arm and held in place between the user's arm and side when transportability is desired.

As shown in FIGS. 9-11, the light source 14 is carried within the housing assembly 12. In one embodiment, as noted previously, the light source 14 comprises one or more LEDs. In particular, as shown, an LED assembly 72 may be provided. Also within the housing assembly 12 is a fan assembly 74 for cooling the LED assembly 72, and a circuit board 76 comprising a controller that controls operation of the light source 14 (or LED assembly 72) and fan assembly 74. The controller on the circuit board 76 is in functional communication with an enabling switch 78 and an on-off switch 80, as will be described. The controller can be any type of processor, including any combination of hardware and/or software. Alternatively, the controller may simply comprise circuit elements for connectivity and operability of the switches 78, 80, light source 14 and fan assembly 74.

In one embodiment, the circuitry embodied by the device 10 may include some or all of the teachings contained in U.S. Pat. No. 6,494,899.

The enabling switch 78 (see FIG. 10) has a contact member 79 for actuating the switch 78. The switch 78 is electrically connected to the circuit board 76 so that, when actuated (e.g., by engagement of contact member 79), an on-off switch 80 positioned within an opening 82 in the gripping surface 56 can function to control the energization of the LED assembly 72 and fan assembly 74. On the other hand, as discussed later, when the enabling switch 78 is not actuated, the on-off switch 80 is disabled so that the LED source 14 cannot be operated.

The on-off switch 80 comprises a switch mechanism 81, and a push button 83. The on-off switch 80 can be of any type known in the art. However, in another embodiment, it is contemplated that the on-off switch 80 can be dispensed with, and the light source 14 will be turned on whenever one of the mode adaptors 22 or 24 engages the contact member 79 of the enabling switch 78. The light source 14, in this embodiment (with no on-off switch 80), is turned off when no mode adaptor is installed.

The energizing source for the assemblies 72 and 74 is a typical AC source communicated with circuit board 76 by an electrical cord 84 which extends through a central portion of the end member 60 of the housing assembly 12. However, any power supply, such as a DC source or battery can also be used.

As best seen in FIG. 10, the housing assembly 12 includes a window 86 in the gripping surface 56 at a position opposed from the opening 82. A display 88, which may take the form of an liquid crystal display (LCD), light emitting diode (LED) display, or other type of display, is disposed in a position to be viewed through window 86. The display 88 may be connected with a timer or clock provided on the circuit board 76 for providing a treatment time of the device, that is, a total "on time" for the light source 14 since the on-off switch 80 has most recently been depressed. In one embodiment, the timer or clock will reset every time the switch 80 is turned off. In another embodiment, the display may also or alternatively show the total usage hours of the LED assembly 72, whether or not the enabling switch 78 has been enabled, and whether or not the on-off switch 80 has been turned on.

The housing parts 58, 60, 62 and 64 and the interior parts 72, 74, 76, 78, 80 and 88 are formed into a unitary construction by gluing or other adhesive means, or in alternate embodiments may be a snap-fit connection, screw connection or any conventional connection.

The LED assembly 72 includes an LED mounting structure 90 having air passages 92 extending therethrough, and is fixedly mounted on the central interior of the lower housing half-shell 64 in a position just above the readout LCD 88. Fixed on the lower housing half-shell 64 adjacent the LED mounting structure 90 is the fan assembly 74 in a position to draw air through the air passages 92 of the LED mounting structure 90. The air drawn through the air passages 92 of the LED mounting structure 90 comes from outside the housing assembly 12 and is drawn through a series of air passages 94 (see FIGS. 9 and 10) formed in an annulus of the end member 58 before it reaches the air passages 92. The air drawn through air passage 92 is circulated out of the housing assembly 12 by the fan assembly 74 through a series of passages 96 formed in an annulus of the end member 60 (see FIG. 9).

The circuit board 76, on-off switch 80 and enabling switch 78 are all initially fixed to the upper housing half-shell 62. After each housing half-shell 62 and 64 have had their respective interior parts fixed thereto, the half-shells can be brought together and glued or otherwise fastened, with the flanges 66 and 68 inter-engaged. It will be noted that when the shells 62 and 64 are moved together, the circuit board 76 is moved into supported relation on a series of upright posts 97 formed integrally with the lower half shell 67 and extending upwardly therefrom (see FIG. 11).

As shown in FIG. 9, the center of the end member 58 defines the connecting site 13 for selectively connecting either one of the adaptors 22 and 24. To this end, at the center of the end member 58, an axially outwardly projecting annular connecting portion 98 is formed having an interior surface 100 defining an adaptor receiving opening 103 therein. The upper rim 101 of connecting portion 98 and the interior surface 100 is defined by an interior a notch or slot 102 formed therein.

As can be appreciated from FIGS. 6-8 and 10, each of the adaptors 22 and 24 includes a tubular forward portion 104 of a size configured to enter within the opening 103 defined by the interior surfaces 100. The rear end of each tubular forward portion 104 is defined by a radially outwardly extending shoulder 106 or stop surface, which transitions into an integral enlarged diameter tubular portion 108 (see FIG. 6). Extending outwardly from the exterior surface of each forward tubular portion 104 in spaced relation to the shoulder 106, is a lug 110 for entering into notch 102.

Figure 6:
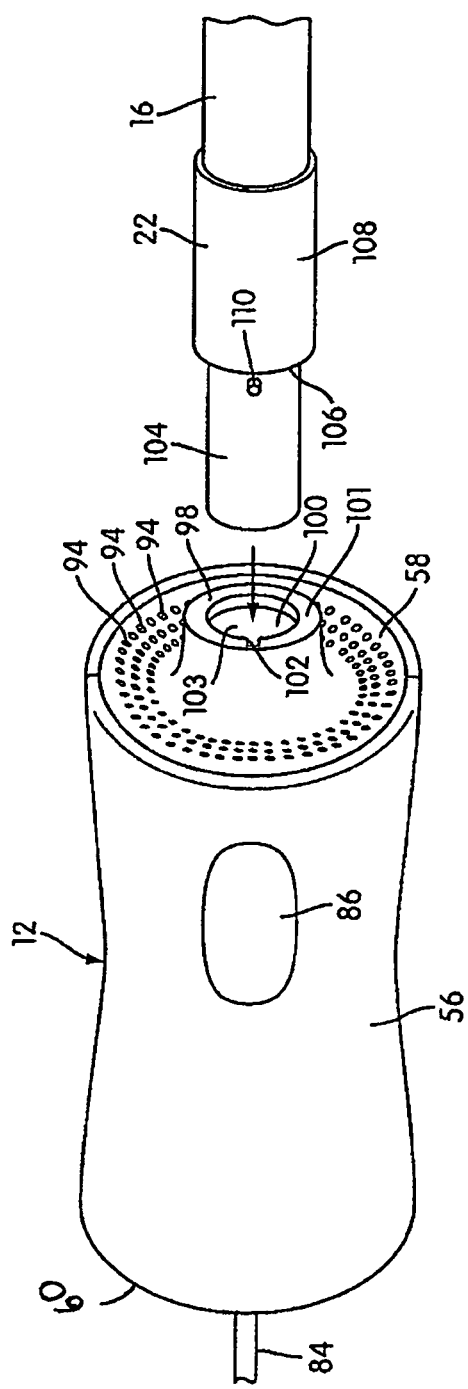
FIG. 6 is a perspective view of the housing assembly of the device of the present invention showing the panel mode adaptor prior to insertion into the housing assembly.
Figure 7:
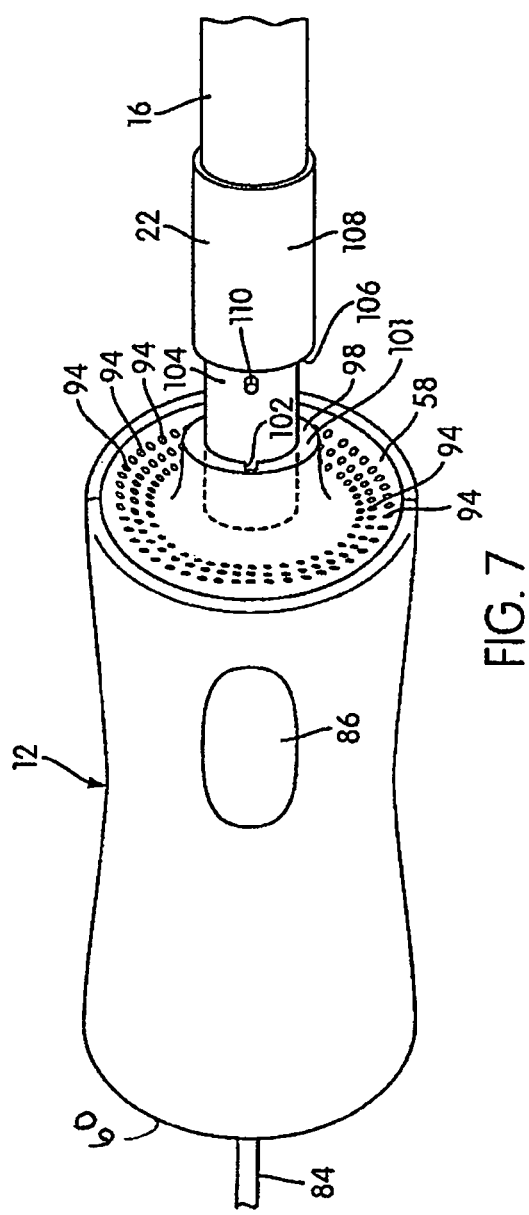
FIG. 7 is a perspective view similar to FIG. 6 showing the panel mode adaptor partially inserted within the housing assembly.
Figure 8:
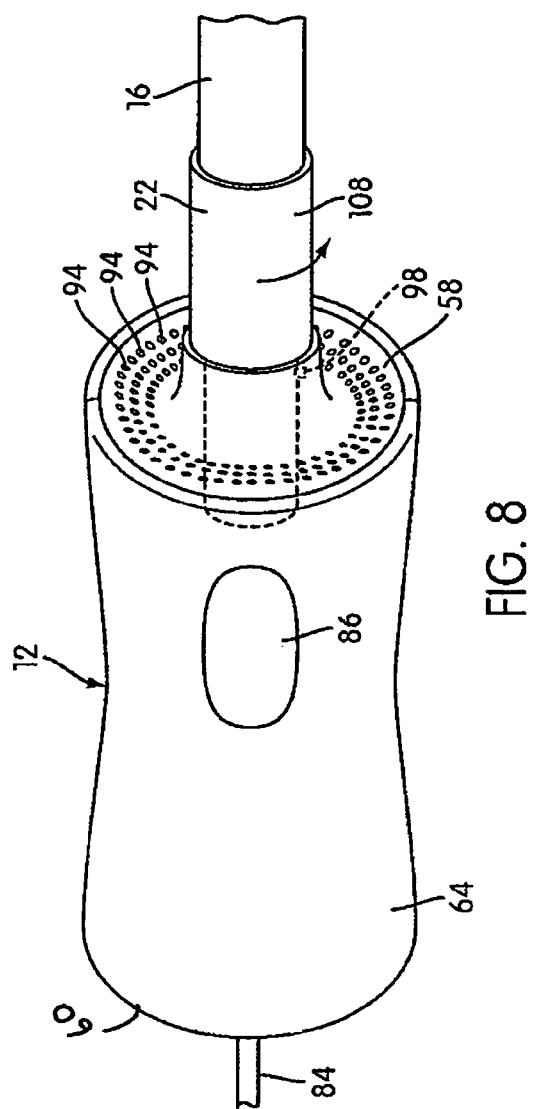
FIG. 8 is a perspective view similar to FIG. 6 showing the panel mode adaptor in connected relation to the housing assembly.

The panel mode adaptor 22 is secured to the proximal end of the light transmitting assembly 16 so that when it is desired to operate the device 10 in the panel mode, the adaptor 22, with the assembly 16 attached, is positioned for insertion through the opening defined by interior surfaces 100 as shown in FIG. 6. The forward portion 104 of the panel mode adaptor 22 is then inserted into the opening 103 defined by the surfaces 100, taking care to align the lug 110 with the notch 102, as shown in FIG. 7. In this position, the adaptor 22 can then be moved inwardly until the shoulder 106 engages the end surface 101 of the protruding connecting portion 98. Finally, by turning the adaptor 22 slightly, the lug 110 will move behind an interior flange (not shown) defined by the surfaces 100 to complete a locked connection, as shown in FIG. 8.

Referring now more particularly to FIG. 10, it can be seen that when either adaptor 22 or 24 is moved into connection with the housing assembly 12, in the manner expressed above, the upper forward end of the forward tubular portion 104 of the adaptor (either 22 or 24) will move through a space within the housing assembly 12 which is occupied by the contact member 79 of an enabling switch 78, so as to engage the contact member 79, to enable operation of the LED assembly 72. Specifically, when both the adaptors 22 and 24 are disengaged with the housing 12, the enabling switch 78 is in a normally disabling condition, and is wired to the circuit board 76 so as to prevent energization of the LED assembly 72 and fan assembly 74, even if the on-off switch 80 is moved into its on position. Consequently, the LED assembly 72 cannot be energized unless one or the other of the adaptors 22 or 24 is in connected relation, as aforesaid, with the housing assembly 12. As a result, the device 10 can be sold with the panel mode adaptor 22 and its panel mode structure 16, 18 and 20 to a care giver for use at home. The spotlight mode adaptor 24 and its suspension structure 26 are typically retained for in hospital use. The in hospital use is quite versatile in that the device 10 can be used in either a panel mode or a spotlight mode.

It should be appreciated that enabling switch 78 can be of any type, such as a contact switch, an electromagnetic switch, an optical switch, a magnetic sensor, proximity sensor, or other sensor, for example.

It should also be appreciated that the enabling switch 78 is optional, and that the device can be manufactured such that the on/off switch 80 has total control over the operation of the LED assembly 72, irrespective of whether one of the adaptors 22 or 24 is connected with the housing 12. Moreover, it should be appreciated that the spotlight mode adaptor 24 is optional, as the light from light source 14 may, in one embodiment, emanate directly from the housing, without passing through the tubular configuration of the adaptor 24. In such an embodiment, it can be appreciated that the housing 10 can be mounted for use in spotlight mode by connecting the suspension structure 26 to a different portion of the housing 12. For example, the suspension structure 26 (which may also be termed a "support structure") may connect with any portion of the housing 12 (e.g., at an intermediate or rear portion of the housing) by any conventional coupling, such as a quick-connect, a quarter turn coupling, a threaded connection, a clamp connection, an interference fit connection, just for example. In addition, the support structure may take an entirely different configuration from suspension structure 26. For example, rather than providing an actual connection with the housing 12, it may simply grasp or clamp onto housing 12, or may simply provide support surfaces on which the housing 12 can rest. It is contemplated that the suspension structure can comprise any mechanical arrangement that allows positioning of the light emitted from the housing assembly 12. It should also be appreciated that in such embodiments, the panel mode adaptor may constitute any structure that facilitates communication of light between the light source 14 and the light pipe 16.

Figure 12:
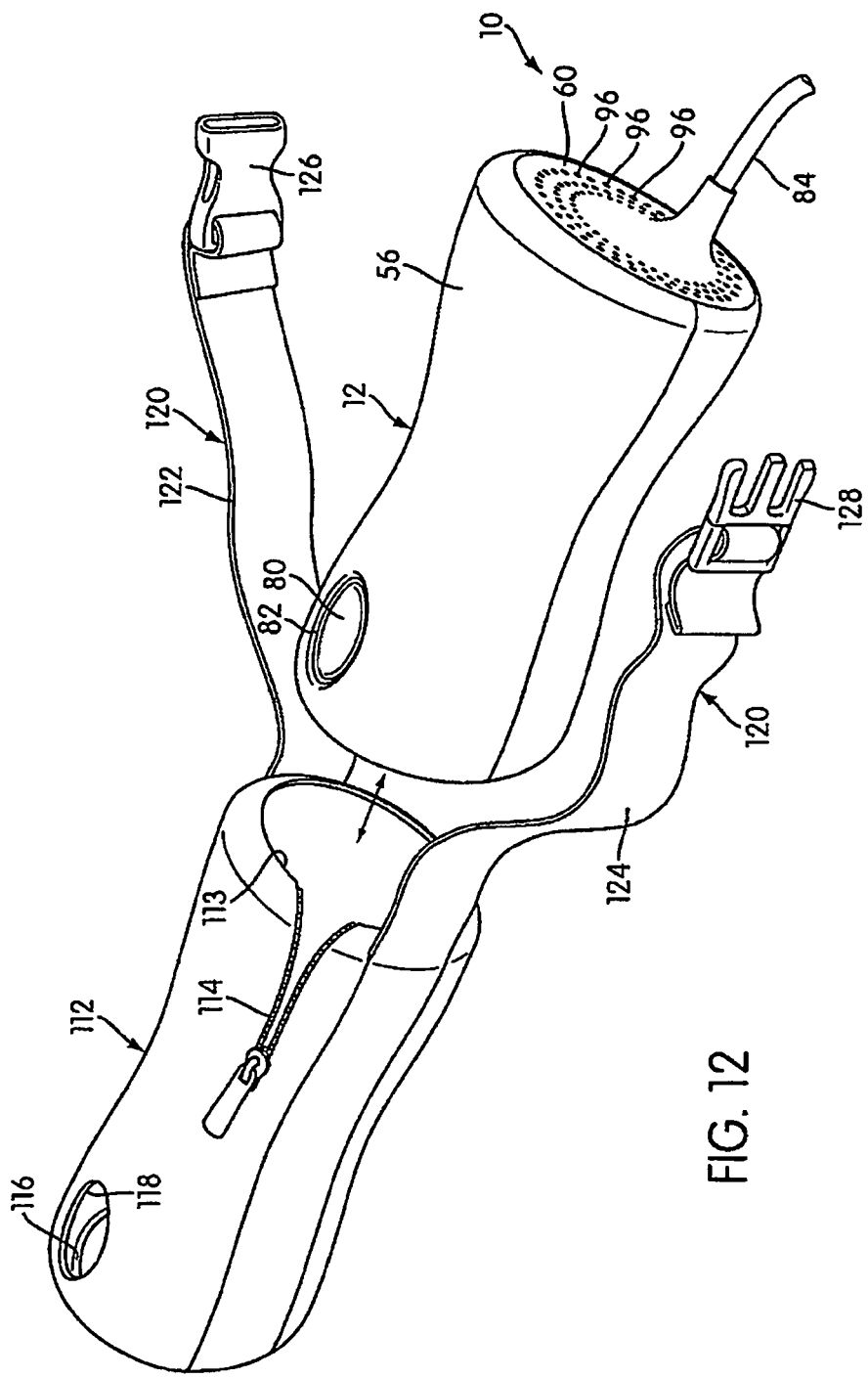
FIGS. 12 and 13 are perspectives view of the housing assembly in a position prior to the insertion thereof into two different embodiments of a bag-like structure embodying one aspect of the present invention.

Referring now more particularly to FIG. 12, there is shown an accessory which can be easily interfaced with the housing assembly 12. The accessory is a bag-like structure, generally indicated at 112. The bag-like structure 112 is formed of a suitable flexible material as, for example, a woven fabric or a flexible plastic. The bag-like structure 112 is configured to securely contain the housing assembly 12 and provide convenient structure for mounting or carrying the housing assembly 12 in a position of operation.

As shown in FIG. 12, a main portion of the bag-like structure 112 is shaped to closely conform to and engage over the gripping surface 56 of the housing assembly 12. One end 113 of the bag-like structure 112 is open for the insertion of the housing assembly therein with its connecting site end first. To aid in positioning the housing assembly 12 through the end 113 of the bag-like structure 112, a zipper assembly 114 may be provided from the end 113 inwardly. The zipper assembly 114 is opened as shown in FIG. 12 to facilitate insertion and is closed after insertion to enable the bag-like structure 112 to closely engage the gripping surface 56 and thereby securely contain the housing assembly 12.

Figure 13:
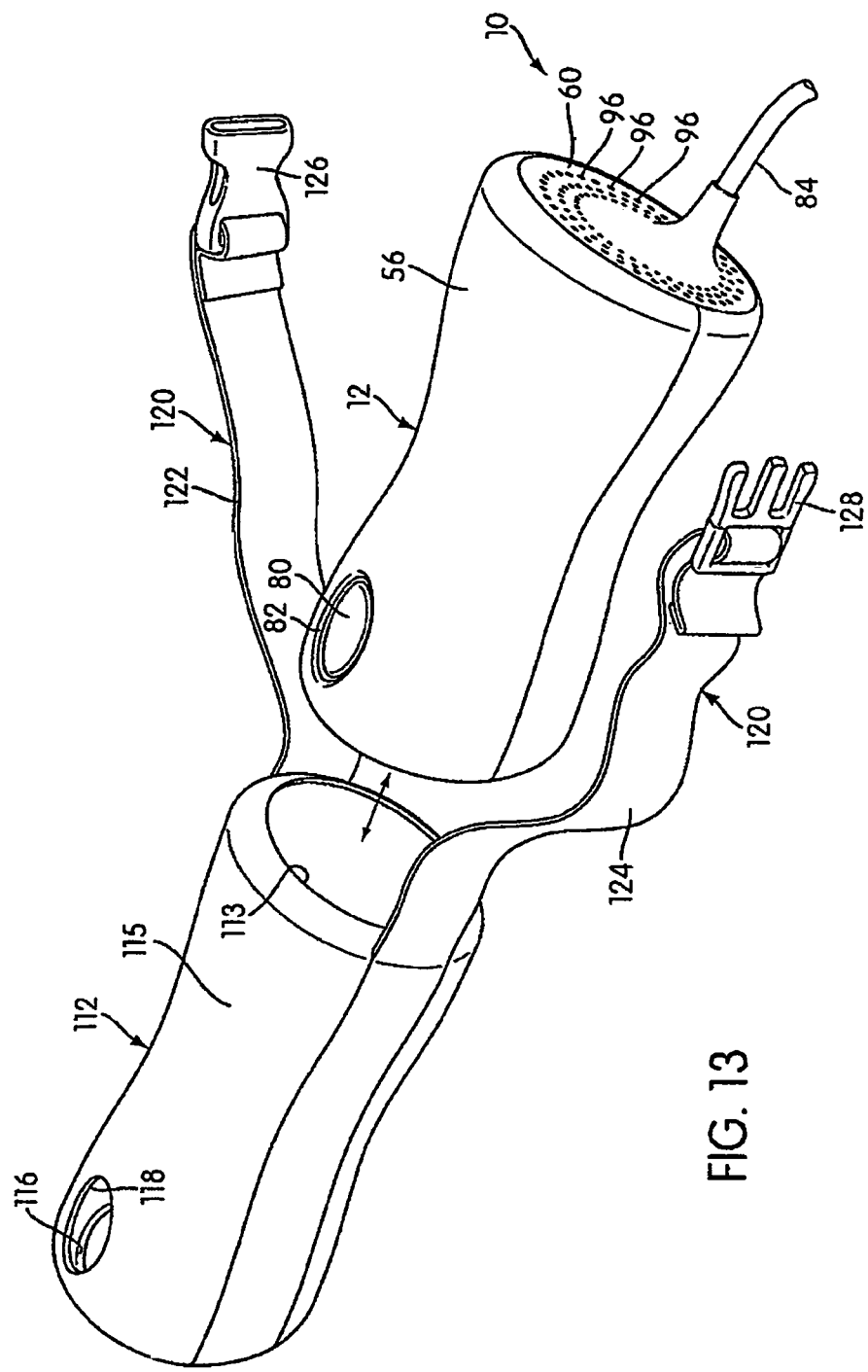

In another embodiment, shown in FIG. 13, no zipper is provided. Rather, the material 115 of bag-like structure 112 is elastic in nature and can be stretched (e.g., like a wet suit) to receive and accommodate the housing assembly 12 in form-fitting relation.

As can be seen from FIG. 12, the end of the bag-like structure 112 opposite from the end having the device receiving opening 113, has an opening 116 therein which is aligned with air passages 94 when the housing assembly 12 is securely contained within the bag-like structure 112. In this way, full air circulation within the housing assembly 12 can be maintained when securely contained within the bag-like structure 112. The opening 116 also allows the adaptors 22 or 24 to be connected with the housing assembly 12 when securely contained in the bag-like structure 112.

FIG. 12 shows that the bag-like structure 112 is formed with a side opening 118, positioned to align with the on-off switch 80. Consequently, the user is enabled to conveniently engage the on-off switch 80 when the housing assembly is securely contained in the bag-like structure. A similar opening (not shown) is provided for the display 88.

FIG. 12 also illustrates that the bag-like structure 112 includes a strap assembly 120 secured to the exterior surface thereof. The strap assembly 120 can be of any desired construction, however, as shown, it is divided into two strap sections 122 and 124. The strap section 122 has one end connected to the exterior surface of the bag-like structure 112 and has a socket connector 126 mounted on a free end thereof. The strap section 124 has one end connected to the exterior of the bag-like structure 112 and its free end mounted with a resilient latch connector 128 capable of being locked into and released from the socket connector 126.

To mount the bag-like structure, the two strap sections 122 and 124 can be disconnected from one another by releasing the operating connectors 126 and 128. The strap sections 122 and 124 can then be placed over a crib rail or the like and then connected together by connectors 126 and 128 to thereby provide support for the contained housing assembly 12 from the crib rail or the like. Such mounting provides most utility when the device 10 is used in the panel mode, but may also accommodate the device 10 when used in the spotlight mode. The strap assembly 120 provides sufficient versatility to enable the user to position the housing assembly 12 of the device 10 at any number of different operating sites. The strap assembly 120 also facilitates carrying of the device 10 between locations. Additional versatility can be provided by making the strap section connection to the bag-like structure 112 of the Velcro type.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. An infant phototherapy device comprising:
   a housing assembly; wherein the housing assembly has an enabling switch; and
   an LED assembly constructed and arranged to emit light within the blue light spectrum, wherein the LED assembly is mounted within the housing assembly between opposite ends thereof so as to emit light from one end of the housing assembly when energized, the housing assembly having a generally cylindrical outer surface including a central portion, wherein the central portion has a smaller diameter than opposite portions of the outer surface,
   wherein the enabling switch of the housing assembly controls energization of the LED assembly when actuated,
   wherein the enabling switch is positioned and configured to be actuated when either one of a pair of mode adaptors is selectively detachably connected to the housing assembly,
   wherein one of the pair of mode adaptors comprises a spotlight mode adaptor which, when selectively detachably connected to the housing assembly, provides an opening therein enabling the phototherapy device to operate in spotlight fashion by emitting light through the opening.

2. An infant phototherapy device as defined in claim 1, wherein the LED assembly, when energized, provides an output intensity greater than 55 mW/cm$^2$/nm, and a lifespan substantially greater than 600 hours.

3. An infant phototherapy device as defined in claim 1, further comprising a suspension structure connected with the spotlight mode adaptor for mounting the housing assembly in a suspended configuration.

4. An infant phototherapy device as defined in claim 1, wherein the housing assembly has an exterior on-off switch controlling the emission of light by the LED assembly positioned to enable a user grasping the outer surface by one hand to actuate the on-off switch.

5. An infant phototherapy device as defined in claim 4, wherein the housing assembly includes end members at opposite ends thereof, and the generally cylindrical outer surface is formed by a pair of complementary half shells inter-engaged with one another and with the aid of the end members.

6. An infant phototherapy device as defined in claim 5, wherein said complementary half-shells have inter-engaging edge flanges which serve to interconnect the complementary half-shells when brought together in cooperating relation.

7. An infant phototherapy device as defined in claim 1, wherein said phototherapy device comprises a display indicating a usage time of the device.

8. An infant phototherapy device as defined in claim 1, wherein one of the pair of mode adaptors comprises a panel mode adaptor connected with an elongated flexible fiber optic light transmitting assembly and a light emitting panel at a distal end thereof, wherein the light emitted from the LED assembly is transmitted by said fiber optic light transmitting assembly to the light emitting panel, wherein the light emitting panel wrappable around an infant being treated.

9. An infant phototherapy device as defined in claim 1, wherein opposite ends of the housing assembly include inlet and outlet air passages therein,
   wherein the LED assembly includes LED mounting structures providing intermediate flow passages between the inlet and outlet passages; and further comprising:
   a fan mounted within the housing assembly in a position to circulate air sequentially through the inlet air passages, intermediate flow passages, and outlet air passages.

10. An infant phototherapy device as defined in claim 9, wherein the infant phototherapy device further includes an LCD readout indicating the LED assembly is in use and the total hours of use.

11. An infant phototherapy device as defined in claim 1, further comprising:
    a bag-like structure constructed and arranged to removably securely contain the housing assembly therein without interfering with the light emitted exteriorly of the housing assembly, wherein
    the bag-like structure includes a mounting strap connected thereto.

12. An infant phototherapy device as defined in claim 11, wherein the housing assembly has an exterior on-off switch controlling the emission of light, the bag-like structure having an opening therein providing access to the on-off switch when the housing assembly is contained therein.

13. An infant phototherapy device as defined in claim 12, wherein the bag-like structure includes a zipper.

14. An infant phototherapy device as defined in claim 8, further comprising:
    the panel mode adaptor, wherein the panel mode adaptor is arranged to be detachably connected with the housing assembly;
    the elongated flexible fiber optic light transmitting assembly;
    the light emitting panel; and
    a suspension structure arranged to suspend the housing assembly, wherein when the panel mode adaptor is disconnected from the housing assembly and the housing assembly is suspended from the suspension structure, light emitted from the housing can be projected onto a patient.

15. The infant phototherapy device according to claim 1, wherein the spotlight mode adaptor has a tubular configuration.

* * * * *